US012698248B2

(12) United States Patent (10) Patent No.: US 12,698,248 B2
Totoki et al. (45) Date of Patent: Aug. 4, 2026

(54) METHOD FOR PRODUCING GUERBET ALCOHOL

(71) Applicant: KAO CORPORATION, Tokyo (JP)

(72) Inventors: Takenori Totoki, Wakayama (JP);
Satoru Onozawa, Wakayama (JP)

(73) Assignee: KAO CORPORATION, Tokyo (JP)

( * ) Notice: Subject to any disclaimer, the term of this
patent is extended or adjusted under 35
U.S.C. 154(b) by 529 days.

(21) Appl. No.: 18/267,995

(22) PCT Filed: Dec. 17, 2021

(86) PCT No.: PCT/JP2021/046664
§ 371 (c)(1),
(2) Date: Jun. 16, 2023

(87) PCT Pub. No.: WO2022/131353
PCT Pub. Date: Jun. 23, 2022

(65) Prior Publication Data
US 2024/0034706 A1      Feb. 1, 2024

(30) Foreign Application Priority Data

Dec. 17, 2020    (JP) ................................. 2020-209234

(51) Int. Cl.
*B01J 23/72*      (2006.01)
*C07C 29/34*      (2006.01)
(52) U.S. Cl.
CPC .............. *C07C 29/34* (2013.01); *B01J 23/72*
(2013.01)
(58) Field of Classification Search
CPC .................................. C07C 29/34; B01J 23/72
See application file for complete search history.

(56) References Cited

U.S. PATENT DOCUMENTS 3,558,716 A * 1/1971 Engelhardt et al. .... C07C 45/74
562/539
2017/0015610 A1 1/2017 Jones et al.

FOREIGN PATENT DOCUMENTS

JP            2-202854  A    8/1990
JP            2-286638  A   11/1990
JP            9-227424  A    9/1997
JP            2669553  B2   10/1997
WO    WO 2019/163640 A1    8/2019

OTHER PUBLICATIONS

International Search Report dated Feb. 22, 2022 for Application No.
PCT/JP2021/046664 with an English translation.
Courtois et al., "Distinct roles of copper in bimetallic copper-
rhodium three-way catalysts deposited on redox supports," Applied
Catalysis B: Environmental, vol. 57, 2005, pp. 63-72.
Extended European Search Report for European Application No.
21906711.3, dated Oct. 29, 2024.

* cited by examiner

*Primary Examiner* — Sikarl A Witherspoon
(74) *Attorney, Agent, or Firm* — Birch, Stewart, Kolasch
& Birch, LLP

(57)      ABSTRACT

A method for producing a Guerbet alcohol, including react-
ing a raw material alcohol having 8 or more and 22 or less
carbon atoms, in the presence of a catalyst (A) containing a
first component and a second component below, having a
molar ratio of the second component with respect to the first
component (second component/first component) of 0.0001
or more and 0.005 or less: first component: copper, and
second component: one kind selected from the group con-
sisting of elements that are elements belonging to Groups 9
to 13 in the fourth to sixth periods of the periodic table,
except copper.

10 Claims, No Drawings

METHOD FOR PRODUCING GUERBET ALCOHOL

FIELD OF THE INVENTION

The present invention relates to a method for producing a Guerbet alcohol.

BACKGROUND OF THE INVENTION

It has been widely known that an aliphatic alcohol is reacted in the presence of a base catalyst or in the presence of a base catalyst and a cocatalyst to produce one molecule of a branched dimerized alcohol (i.e., a Guerbet alcohol) through removal of one molecule of water from two molecules of the alcohol, and the reaction has been referred to as Guerbet reaction.

In the case where a primary alcohol is used as the raw material alcohol as an example, it has been estimated that the reaction mechanism of the Guerbet reaction is constituted by the following elementary reactions (1) to (4):

(1) formation of an aldehyde through dehydrogenation of the alcohol, (2) formation of an α,β-unsaturated aldehyde through aldol condensation of the aldehyde, (3) formation of an allyl alcohol through reduction of the α,β-unsaturated aldehyde, and (4) formation of a Guerbet alcohol through reduction of the allyl alcohol.

In the elementary reactions (1) to (4), various investigations have been reported for the kind and the amount of the base catalyst used, the kind and the amount of the cocatalyst used, and the like, for such purposes as the suppression of the side reaction, the enhancement of the reaction rate, the enhancement of the yield and the enhancement of the quality of the Guerbet alcohol obtained, and the like.

For example, PTL 1 describes a method for producing a branched dimerized alcohol through reaction of an alcohol having 3 to 26 carbon atoms in the presence of (a) a catalyst formed of an alkaline substance and (b) a catalyst which is copper, a fourth period transition metal element (e.g., nickel, chromium, cobalt, manganese, iron, and zinc), and a Group 8 platinum group element (e.g., platinum, palladium, ruthenium, and rhodium) in which the ratio copper/fourth period transition metal element is 1/9 to 9/1 (molar ratio), and the ratio Group 8 platinum group element/(copper+fourth period transition metal element) is 0.001 to 0.1 (molar ratio).

CITATION LIST

Patent Literature

PTL 1: JP 2-286638 A

SUMMARY OF THE INVENTION

However, according to the method for producing a branched dimerized alcohol described in PTL 1, it is stated that the reaction time can be shortened, and the yield and the selectivity of the alcohol formed can be enhanced, as compared to the ordinary methods, but there is room for improvement from the standpoint of the shortening of the reaction time and the enhancement of the yield of the Guerbet alcohol formed.

Under the circumstances, a problem to be solved by the present invention is to provide a method for producing a Guerbet alcohol, capable of shortening the reaction time and enhancing the yield of the Guerbet alcohol formed.

The present inventors have found that the problem can be solved by reacting a raw material alcohol having 8 or more and 22 or less carbon atoms in the presence of a particular catalyst (A).

The present invention relates to the following items [1] and [2].

[1] A method for producing a Guerbet alcohol, including reacting a raw material alcohol having 8 or more and 22 or less carbon atoms, in the presence of a catalyst (A) containing a first component and a second component below, having a molar ratio of the second component with respect to the first component (second component/ first component) of 0.0001 or more and 0.005 or less:

first component: copper, and second component: one kind selected from the group consisting of elements that are elements belonging to Groups 9 to 13 in the fourth to sixth periods of the periodic table, except copper.

[2] A catalyst used for a method for producing a Guerbet alcohol, including a first component and a second component below, having a molar ratio of the second component with respect to the first component (second component/first component) of 0.0001 or more and 0.005 or less:

first component: copper, and second component: one kind selected from the group consisting of elements that are elements belonging to Groups 9 to 13 in the fourth to sixth periods of the periodic table, except copper.

According to the present invention, a method for producing a Guerbet alcohol, capable of shortening the reaction time and enhancing the yield of the Guerbet alcohol formed can be provided.

DETAILED DESCRIPTION OF THE INVENTION

The method for producing a Guerbet alcohol of the present invention includes reacting a raw material alcohol having 8 or more and 22 or less carbon atoms, in the presence of a catalyst (A) containing a first component and a second component below, having a molar ratio of the second component with respect to the first component (second component/first component) of 0.0001 or more and 0.005 or less:

first component: copper, and second component: one kind selected from the group consisting of elements that are elements belonging to Groups 9 to 13 in the fourth to sixth periods of the periodic table, except copper.

The present invention exerts an effect of shortening the reaction time and enhancing the yield of the Guerbet alcohol formed. The mechanism therefor is not clear, but can be considered as follows.

In the formation process of an aldehyde through dehydrogenation of the raw material alcohol in the reaction mechanism of the Guerbet reaction, with the catalyst (A) containing the first and second components, the dehydrogenation reaction of the raw material alcohol proceeds on the surface of copper as the first component, generating hydrogen that is in a state of coordinating on the surface of the copper, and then hydrogen on the surface of the copper migrates to the surface of the second component. As a result, the surface of copper as the first component of the catalyst (A) becomes coordinative unsaturation, and the regeneration rate of the vacant sites of copper is increased to accelerate the dehydrogenation reaction of the raw material alcohol, as compared to a catalyst containing no second component.

[Raw Material Alcohol]

In the method for producing a Guerbet alcohol of the present invention, an alcohol having 8 or more and 22 or less carbon atoms (which may be hereinafter referred simply to as a "raw material alcohol") is used.

The number of carbon atoms of the raw material alcohol is 8 or more, preferably 9 or more, more preferably 10 or more, and further preferably 11 or more, and is 22 or less, preferably 20 or less, more preferably 18 or less, further preferably 16 or less, and still further preferably 15 or less, from the standpoint of the yield of the Guerbet alcohol.

One kind of the raw material alcohol may be used alone, or two or more kinds thereof may be used in combination.

Examples of the raw material alcohol include a primary aliphatic alcohol and a secondary aliphatic alcohol, among which a primary aliphatic alcohol is preferred, a primary aliphatic alcohol having 8 or more and 18 or less carbon atoms is more preferred, a saturated linear primary aliphatic alcohol having 8 or more and 18 or less carbon atoms is more preferred, a saturated linear primary aliphatic alcohol having 10 or more and 16 or less carbon atoms is further preferred, a saturated linear primary aliphatic alcohol having 11 or more and 15 or less carbon atoms is still further preferred, and a saturated linear primary aliphatic alcohol having 12 or more and 14 or less carbon atoms is still more further preferred, from the standpoint of the yield of the Guerbet alcohol.

Specific examples of the primary aliphatic alcohol include a saturated linear alcohol, such as 1-octanol (C8), 1-nonanol (C9), 1-decanol (d10), 1-undecanol (C11), 1-dodecanol (C12), 1-tridecanol (C13), 1-tetradecanol (C14), 1-pentadecanol (d15), 1-hexadecanol (C16), 1-heptadecanol (C17), 1-octadecanol (C18), 1-nonadecanol (C19), 1-eicosanol (C20), 1-heneicosanol (C21), and 1-docosanol (C22); a saturated alicyclic alcohol, such as cyclohexaneethanol (C8), cyclohexanepropanol (C9), and cyclohexanebutanol (d10); and an unsaturated alcohol, such as citronellol (C10) and oleyl alcohol (C18).

Specific examples of the secondary aliphatic alcohol include a saturated linear alcohol, such as 2-octanol (C8), 2-nonanol (C9), 2-decanol (d10), 2-undecanol (C11), 2-dodecanol (C12), 2-tridecanol (C13), 2-tetradecanol (C14), 2-pentadecanol (CM), 2-hexadecanol (C16), 2-heptadecanol (C17), 2-octadecanol (C18), 2-nonadecanol (C19), 2-eicosanol (C20), 2-heneicosanol (C21), and 2-docosanol (C22).

[Catalyst (A)]

In the method for producing a Guerbet alcohol of the present invention, the catalyst (A) containing the particular components at the particular molar ratio is used, and the catalyst (A) that includes a carrier having the particular components supported thereon may also be used. The use of the catalyst (A) can shorten the reaction time, and can enhance the yield of the Guerbet alcohol formed.

The catalyst (A) used in the present invention is a catalyst containing the first component and the second component shown below, and may also be a catalyst that includes a carrier having the first component and the second component shown below supported thereon:

first component: copper, and second component: one kind selected from the group consisting of elements that are elements belonging to Groups 9 to 13 in the fourth to sixth periods of the periodic table, except copper.

(First Component)

The first component of the catalyst (A) is not particularly limited, as far as the component is copper (Cu), and an oxide thereof may also be used.

The content of the first component (Cu) contained in the catalyst (A) is preferably 6% by mass or more, more preferably 8% by mass or more, further preferably 10% by mass or more, and still further preferably 15% by mass or more, from the standpoint of the yield of the Guerbet alcohol, and is preferably 60% by mass or less, more preferably 50% by mass or less, further preferably 45% by mass or less, still further preferably 40% by mass or less, and still more further preferably 35% by mass or less, from the standpoint of the yield of the Guerbet alcohol and the economic efficiency.

The content of the first component contained in the catalyst (A) can be obtained specifically through measurement in the manner described in the examples.

The average primary particle diameter of the first component (Cu) contained in the catalyst (A) is preferably 0.2 nm or more, more preferably 1 nm or more, further preferably 3 nm or more, and still further preferably 10 nm or more, and is preferably 120 nm or less, more preferably 100 nm or less, further preferably 80 nm or less, and still further preferably 60 nm or less, from the standpoint of the yield of the Guerbet alcohol.

The average primary particle diameter of the first component (Cu) contained in the catalyst (A) can be obtained specifically through measurement in the manner described in the examples.

(Second Component)

The second component of the catalyst (A) is not particularly limited, as far as the component is one kind selected from the group consisting of elements that are elements belonging to Groups 9 to 13 in the fourth to sixth periods of the periodic table, except copper, and an oxide thereof may also be used.

In the second component, one kind selected from the group consisting of the elements except copper and zinc is preferred, and one kind selected from gallium (Ga), rhodium (Rh), palladium (Pd), iridium (Ir), and platinum (Pt) is more preferred.

The content of the second component contained in the catalyst (A) is preferably 0.0005% by mass or more, more preferably 0.0006% by mass or more, further preferably 0.0008% by mass or more, still further preferably 0.001% by mass or more, still more further preferably 0.0025% by mass or more, and even further preferably 0.005% by mass or more, and is preferably 1% by mass or less, more preferably 0.8% by mass or less, further preferably 0.6% by mass or less, still further preferably 0.5% by mass or less, still more further preferably 0.28% by mass or less, and even further preferably 0.1% by mass or less, from the standpoint of the yield of the Guerbet alcohol.

The content of the second component contained in the catalyst (A) can be obtained specifically through measurement in the manner described in the examples.

(Third Component)

The catalyst (A) of the present invention may contain a third component other than the first component and the second component in such a range that does not impair the effects of the present invention.

Examples of the third component of the catalyst (A) include at least one kind selected from the group consisting of elements that are elements belonging to Groups 3 to 13 in the fourth to sixth periods of the periodic table, except copper and the second component.

The content of the third component contained in the catalyst (A) is preferably 10% by mass or less, more preferably 5% by mass or less, further preferably 3% by mass or less, and still further preferably 0% by mass.

The content of the third component contained in the catalyst (A) can be obtained through measurement in the same manner as in the first component and second component described above.

(Carrier)

The catalyst (A) is preferably a catalyst including a carrier having the first component and the second component supported thereon from the standpoint of the productivity.

The carrier of the catalyst (A) is not particularly limited, as far as the carrier can support the first component and the second component.

Examples of the carrier of the catalyst (A) include a carbon material, such as activated carbon, nano carbon, and carbon black; and an inorganic material, such as aluminum oxide, iron oxide, copper oxide, titanium oxide, zirconium oxide, zeolite, cerium oxide, and hydrotalcite. Among these, the carrier of the catalyst (A) is preferably at least one kind selected from the group consisting of aluminum oxide, activated carbon, titanium oxide, zirconium oxide, zeolite, cerium oxide, and hydrotalcite, among which at least one kind selected from the group consisting of aluminum oxide, zirconium oxide, and hydrotalcite is more preferred.

The shape of the carrier is not particularly limited, and is generally in the form of powder, the median diameter (d50) of which is generally 1 to 300 in, and the shape thereof may be other shapes derived from powder depending on necessity.

The total content of the first component and the second component contained in the catalyst (A) including the carrier is preferably 6% by mass or more, more preferably 8% by mass or more, and further preferably 10% by mass or more, and is preferably 55% by mass or less, more preferably 50% by mass or less, further preferably 45% by mass or less, and still further preferably 41% by mass or less, from the standpoint of the yield of the Guerbet alcohol.

The catalyst (A) may contain the first component and the second component with no carrier included. The total content of the first component and the second component contained in the catalyst (A) including no carrier is preferably 50% by mass or more, more preferably 60% by mass or more, further preferably 65% by mass or more, and still further preferably 70% by mass or more, from the standpoint of the yield of the Guerbet alcohol.

The molar ratio of the second component with respect to the first component (second component/first component) in the catalyst (A) is 0.0001 or more, preferably 0.000125 or more, more preferably 0.00015 or more, and further preferably 0.0003 or more, and is 0.005 or less, preferably 0.004 or less, and more preferably 0.003 or less, from the standpoint of the yield of the Guerbet alcohol.

The shape of the catalyst (A) is not particularly limited, and examples thereof include powder, granules, noodle-like form, and pellets. The shapes including granules, noodle-like form, and pellets can be produced through granulation or molding the catalyst (A) in the form of powder by a known method.

In the case where the catalyst (A) is in the form of powder, the median diameter (d50) of the catalyst (A) is preferably 1 μm or more, more preferably 3 μm or more, further preferably 5 μm or more, and still further preferably 7 μm or more, from the standpoint of the recoverability, and is preferably 300 μm or less, more preferably 200 μm or less, further preferably 100 μm or less, and still further preferably 30 μm or less, from the standpoint of the yield of the Guerbet alcohol. The median diameter (d50) of the catalyst (A) can be measured with a laser diffraction/scattering particle size distribution analyzer "LA-920" (produced by Horiba, Ltd.). The measurement may be performed after dispersing 0.05 g of the catalyst (A) in ion exchanged water as the measurement solvent under stirring (stirring rate: level 4), and the median diameter (d50) is calculated with an appropriate relative refractive index.

In the case where the catalyst (A) is in the form of granules, the average particle diameter of the catalyst (A) is preferably 0.2 mm or more, more preferably 0.4 mm or more, and further preferably 0.6 mm or more, from the standpoint of the recoverability, and is preferably 2.0 mm or less, more preferably 1.3 mm or less, and further preferably 0.8 mm or less, from the standpoint of the yield of the Guerbet alcohol. The average particle diameter of the catalyst (A) herein means the arithmetic average particle diameter, and can be obtained with a vernier caliper. The number of the granules for obtaining the average particle diameter may be 30 granules randomly selected.

In the case where the catalyst (A) is in the noodle-like form, the average diameter of the catalyst (A) is preferably 1.0 mm or more, more preferably 1.2 mm or more, and further preferably 1.4 mm or more, from the standpoint of the strength of the catalyst, and is preferably 2.5 mm or less, more preferably 2.0 mm or less, and further preferably 1.5 mm or less, from the standpoint of the yield of the Guerbet alcohol. The average diameter of the catalyst (A) herein means the arithmetic average diameter, and can be obtained with a vernier caliper. The number of the noodles for obtaining the average diameter may be 30 noodles randomly selected.

In the case where the catalyst (A) is in the noodle-like form, the average length of the catalyst (A) is preferably 2 mm or more, and more preferably 3 mm or more, from the standpoint of the strength of the catalyst, and is preferably 8 mm or less, more preferably 6 mm or less, and further preferably 4 mm or less, from the standpoint of the homogeneity in packing and the yield of the Guerbet alcohol. The average length of the catalyst (A) herein means the arithmetic average length, and can be obtained with a vernier caliper. The number of the noodles for obtaining the average length may be 30 noodles randomly selected.

In the case where the catalyst (A) is in the form of pellets, the average diameter and the average height of the catalyst (A) each are preferably 1.5 mm or more, more preferably 2.0 mm or more, and further preferably 2.5 mm or more, from the standpoint of the strength of the catalyst, and is preferably 5.0 mm or less, more preferably 4.0 mm or less, and further preferably 3.0 mm or less, from the standpoint of the yield of the Guerbet alcohol. The average diameter and the average height of the catalyst (A) herein mean the arithmetic average diameter and the arithmetic average height respectively, and can be obtained with a vernier caliper. The number of the pellets for obtaining the average diameter or the average height may be 30 pellets randomly selected.

(Preparation of Catalyst (A))

The catalyst (A) used in the present invention may be prepared by a known method, such as a precipitation method, an impregnation method, an ion exchange method, an alloying method, and an adsorption method.

The catalyst (A) may be prepared preferably by a method of supporting the first component by the precipitation method on the carrier, and then supporting the second component by the impregnation method on the carrier having the first component supported thereon.

The precipitation method for supporting the first component on the carrier may be performed, for example, in the following manner.

A first component-containing water-soluble salt is dissolved in ion exchanged water to prepare an aqueous solution containing the first component. Separately, an alkali aqueous solution containing an alkali component, such as sodium carbonate, and a slurry containing a component to be the carrier, such as zirconium oxide, are prepared, respectively. Subsequently, the aqueous solution containing the first component is added dropwise to the slurry, simultaneously the alkali aqueous solution is added dropwise thereto, and the solutions are added dropwise thereto for a prescribed period of time while retaining a prescribed pH of the slurry for insolubilizing and depositing the first component as a carbonate salt or a hydroxide, so as to provide a solid matter including the carrier having the carbonate salt or the hydroxide of the first component attached thereto. The solid matter is repeatedly subjected to an operation including filtration and washing, and baked at a prescribed temperature for a prescribed period of time, so as to provide a baked material including the carrier having the first component supported thereon.

The impregnation method for supporting the second component on the carrier having the first component supported thereon may be performed, for example, in the following manner.

A second component-containing solution or a second component-containing compound is dissolved in ion exchanged water or an organic solvent, to which the baked material of the solid matter including the carrier having the first component supported thereon is added, and the mixture is concentrated until the liquid phase disappears, for example, through depressurization or heating under stirring, then dried at a prescribed temperature, and further baked at a prescribed temperature for a prescribed period of time, so as to provide the catalyst (A) as a baked material including the carrier having the first and second components supported thereon.

The baking temperature for providing the baked material including the carrier having the first component supported thereon and the baked material including the carrier having the first and second components supported thereon is preferably 300° C. or more, more preferably 350° C. or more, and further preferably 400° C. or more, and is preferably 900° C. or less, more preferably 850° C. or less, and further preferably 800° C. or less, from the standpoint of the yield of the Guerbet alcohol.

The baking time for providing the baked material including the carrier having the first component supported thereon and the baked material including the carrier having the first and second components supported thereon is preferably 1 hour or more, more preferably 2 hours or more, and further preferably 3 hours or more, and is preferably 10 hours or less, more preferably 7 hours or less, and further preferably 5 hours or less, from the standpoint of the yield of the Guerbet alcohol.

The baking atmosphere for providing the baked material including the carrier having the first component supported thereon and the baked material including the carrier having the first and second components supported thereon is not particularly limited, examples of which include an inert gas atmosphere, such as nitrogen, an oxidizing atmosphere, such as air, and a reducing atmosphere, such as hydrogen, and among these, an oxidizing atmosphere, such as air, is preferred from the standpoint of the yield of the Guerbet alcohol. The baking atmosphere may be either a close state or an open state.

[Base Catalyst (B)]

In the method for producing a Guerbet alcohol of the present invention, a base catalyst (B) is preferably used with the catalyst (A).

The use of the base catalyst (B) with the catalyst (A) can facilitate the shortening of the reaction time and the enhancement of the yield of the Guerbet alcohol formed.

Examples of the base catalyst (B) include an alkali metal and an alkaline earth metal, and hydrides, hydroxides, carbonates, hydrogen carbonates, and alkoxides thereof.

Specific examples of hydrides, hydroxides, carbonates, hydrogen carbonates, and alkoxide compounds of an alkali metal and an alkaline earth metal include an alkali metal hydroxide, such as LiOH, NaOH, KOH, RbOH, and CsOH; an alkali metal carbonate, such as $Li_2CO_3$, $Na_2CO_3$, $K_2CO_3$, $Rb_2CO_3$, $Cs_2CO_3$; an alkali metal hydrogen carbonate, such as $LiHCO_3$, $NaHCO_3$, $KHCO_3$, $RbHCO_3$, $CsHCO_3$; an alkali metal alkoxide compound, such as sodium methoxide, sodium ethoxide, sodium t-butoxide, potassium methoxide, potassium ethoxide, and potassium t-butoxide; and an alkaline earth metal hydroxide, such as $Mg(OH)_2$ and $Ca(OH)_2$.

In the base catalyst (B), an alkali metal hydroxide, such as LiOH, NaOH, KOH, RbOH, and CsOH; and an alkali metal alkoxide compound, such as sodium methoxide, sodium ethoxide, sodium t-butoxide, potassium methoxide, potassium ethoxide, and potassium t-butoxide, all of which are strong bases, are preferred from the standpoint of the yield of the Guerbet alcohol, among which NaOH and KOH are more preferred, and KOH is further preferred, from the standpoint of the versatility and the economic efficiency.

One kind of the base catalyst (B) may be used alone, or two or more kinds thereof may be used in combination.

The base catalyst (B) may not be supported on a carrier.

The amount of the base catalyst (B) per 100 parts by mol in total of the amount of the raw material alcohol is preferably 0.1 part by mol or more, more preferably 0.2 part by mol or more, and further preferably 0.3 part by mol or more, from the standpoint of the yield of the Guerbet alcohol, and is preferably 7 parts by mol or less, more preferably 5 parts by mol or less, and further preferably 3 parts by mol or less, from the standpoint of the selectivity.

[Guerbet Reaction]

In the method for producing a Guerbet alcohol of the present invention, a raw material alcohol having 8 or more and 22 or less carbon atoms is reacted (dehydration condensation reaction (Guerbet reaction)) in the presence of the catalyst (A) including the carrier having the particular components supported thereon, so as to form a Guerbet alcohol.

The catalyst (A) may be a catalyst that does not include the carrier for supporting.

The use mode of the catalyst (A) for the Guerbet reaction is not particularly limited, and may be either suspended bed reaction or fixed bed reaction, which may be appropriately selected depending on the catalyst activity, the reaction scale, and the like. The material of the reaction equipment used for the Guerbet reaction may be a stainless steel (such as SUS201, SUS202, SUS301, SUS302, SUS303, SUS304, SUS305, SUS316, SUS317, SUS329J1, SUS403, SUS405, SUS420, SUS430, SUS430LX, and SUS630), and may be glass.

The reaction mode of the method for producing a Guerbet alcohol of the present invention may be either a batch system, a semi-batch system, or a continuous system.

In the case where the reaction mode is suspended bed reaction, a batch system or a semi-batch system is preferred from the standpoint of the operability, and the amount of the catalyst (A) per 100 parts by mass in total of the amount of the raw material alcohol is preferably 0.01 part by mass or more, more preferably 0.05 part by mass or more, and further preferably 0.1 part by mass or more, from the standpoint of the yield of the Guerbet alcohol, and is preferably 10 parts by mass or less, more preferably 5 parts by mass or less, and further preferably 1 part by mass or less, from the standpoint of the economic efficiency.

In the case where the reaction mode is fixed bed reaction, a continuous system is preferred from the standpoint of the yield of the Guerbet alcohol, and the amount of the catalyst (A) per 100 parts by mass in total of the amount of the raw material alcohol is preferably 10 parts by mass or more, more preferably 15 parts by mass or more, further preferably 25 parts by mass or more, and still further preferably 50 parts by mass or more, from the standpoint of the yield of the Guerbet alcohol, and is preferably 4,000 parts by mass or less, more preferably 2,500 parts by mass or less, further preferably 1,000 parts by mass or less, and still further preferably 500 parts by mass or less, from the standpoint of the economic efficiency.

The reaction temperature of the Guerbet reaction may be appropriately determined in consideration of the boiling point of the raw material alcohol, is preferably 180° C. or more, more preferably 190° C. or more, further preferably 200° C. or more, and still further preferably 220° C. or more, from the standpoint of the yield of the Guerbet alcohol, and is preferably 300° C. or less, more preferably 280° C. or less, and further preferably 260° C. or less, from the standpoint of the selectivity.

The reaction time of the Guerbet reaction may be appropriately determined depending on the reaction temperature and the kind of the raw material alcohol, and the reaction time in the batch system is generally 1 hour or more from the standpoint of the yield of the Guerbet alcohol, and is preferably 20 hours or less, and more preferably 10 hours or less, from the standpoint of the productivity. The LHSV (liquid hourly space velocity) in the continuous system is preferably 10/hr or less, more preferably 7/hr or less, further preferably 5/hr or less, and still further preferably 3/hr or less, from the standpoint of the yield of the Guerbet alcohol, and is preferably 0.03/hr or more, more preferably 0.05/hr or more, further preferably 0.1/hr or more, and still further preferably 0.2/hr or more, from the standpoint of the productivity.

The pressure of the gas phase in reaction of the Guerbet reaction may be either reduced pressure, ordinary pressure, or increased pressure, may be reduced pressure from the standpoint of the yield of the Guerbet alcohol, and may be ordinary pressure from the standpoint of the operability and the economic efficiency.

In the Guerbet reaction, it is preferred from the standpoint of the yield of the Guerbet alcohol that an inert gas is introduced to the reaction system, and the inert gas is allowed to flow as a carrier gas. The inert gas is not particularly limited, examples of which include nitrogen gas and argon gas, and among these, nitrogen gas is preferably used.

The inert gas may be allowed to flow by a method of flowing in the upper part of the reaction liquid, a method of bubbling in the reaction liquid, and the like.

The flow rate of the inert gas in increasing the temperature until reaching the reaction temperature is not particularly limited, and the flow rate per 1 kg of the reaction liquid is preferably 0.5 L/hr or more, more preferably 3 L/hr or more, and further preferably 8 L/hr or more, from the standpoint of the yield of the Guerbet alcohol, and is preferably 30 L/hr or less, more preferably 25 L/hr or less, and further preferably 20 L/hr or less, from the standpoint of the economic efficiency.

The flow rate of the inert gas in the reaction after reaching the reaction temperature is not particularly limited, and the flow rate per 1 kg of the reaction liquid is preferably 0.02 L/hr or more, more preferably 0.08 L/hr or more, and further preferably 0.1 L/hr or more, from the standpoint of the yield of the Guerbet alcohol, and is preferably 10 L/hr or less, more preferably 5 L/hr or less, and further preferably 2 L/hr or less, from the standpoint of the economic efficiency.

The Guerbet alcohol formed in the production method of the present invention is determined depending on the kind of the raw material alcohol used, may be saturated or unsaturated, may be primary or secondary, and may have a cyclic structure.

The number of carbon atoms of the Guerbet alcohol formed in the production method of the present invention is preferably 16 or more, more preferably 18 or more, and further preferably 20 or more, and is preferably 44 or less, more preferably 40 or less, and further preferably 36 or less, from the standpoint of the yield of the Guerbet alcohol.

The production method of the present invention can shorten the reaction time and can enhance the yield of the Guerbet alcohol formed. The Guerbet alcohol obtained by the production method of the present invention can be applied directly to various purposes, and may also be applied after purification by a distillation operation or the like depending on necessity. A Guerbet alcohol is useful as a raw material or an intermediate material of surfactants, textile oil agents, fabric softeners, cosmetics, medical drugs, lubricating oils, and the like. From the standpoint of the application to these purposes, the purity of the Guerbet alcohol is preferably 95% by mass or more, more preferably 97% by mass or more, and further preferably 98% by mass or more.

In addition to the aforementioned embodiments, the present invention relates to the following methods for producing a Guerbet alcohol.

<1> A method for producing a Guerbet alcohol, including reacting a raw material alcohol having 8 or more and 22 or less carbon atoms, in the presence of a catalyst (A) containing a first component and a second component below, having a molar ratio of the second component with respect to the first component (second component/first component) of 0.0001 or more and 0.005 or less:

first component: copper, and second component: one kind selected from the group consisting of elements that are elements belonging to Groups 9 to 13 in the fourth to sixth periods of the periodic table, except copper.

<2> The method for producing a Guerbet alcohol according to the item <1>, wherein the second component of the catalyst (A) is preferably one kind selected from gallium (Ga), rhodium (Rh), palladium (Pd), iridium (Ir), and platinum (Pt).

<3> The method for producing a Guerbet alcohol according to the item <1> or <2>, wherein the molar ratio of the second component with respect to the first component (second component/first component) in the catalyst (A) is preferably 0.0001 or more and 0.005 or less.

<4> The method for producing a Guerbet alcohol according to any one of the items <1> to <3>, wherein the molar ratio of the second component with respect to the first component (second component/first component) in the catalyst (A) is preferably 0.000125 or more and 0.005 or less.

<5> The method for producing a Guerbet alcohol according to any one of the items <1> to <4>, wherein the molar ratio of the second component with respect to the first component (second component/first component) in the catalyst (A) is preferably 0.00015 or more and 0.004 or less.

<6> The method for producing a Guerbet alcohol according to any one of the items <1> to <5>, wherein the molar ratio of the second component with respect to the first component (second component/first component) in the catalyst (A) is preferably 0.0003 or more and 0.003 or less.

<7> The method for producing a Guerbet alcohol according to any one of the items <1> to <6>, wherein the content of the first component contained in the catalyst (A) is preferably 6% by mass or more and 50% by mass or less.

<8> The method for producing a Guerbet alcohol according to any one of the items <1> to <7>, wherein the content of the first component contained in the catalyst (A) is preferably 8% by mass or more and 45% by mass or less.

<9> The method for producing a Guerbet alcohol according to any one of the items <1> to <8>, wherein the content of the first component contained in the catalyst (A) is preferably 10% by mass or more and 40% by mass or less.

<10> The method for producing a Guerbet alcohol according to any one of the items <1> to <9>, wherein the content of the first component contained in the catalyst (A) is preferably 15% by mass or more and 35% by mass or less.

<11> The method for producing a Guerbet alcohol according to any one of the items <1> to <10>, wherein the average primary particle diameter of the first component contained in the catalyst (A) is preferably 3 nm or more and 100 nm or less.

<12> The method for producing a Guerbet alcohol according to any one of the items <1> to <11>, wherein the average primary particle diameter of the first component contained in the catalyst (A) is preferably 10 nm or more and 80 nm or less.

<13> The method for producing a Guerbet alcohol according to any one of the items <1> to <12>, wherein the average primary particle diameter of the first component contained in the catalyst (A) is preferably 10 nm or more and 60 nm or less.

<14> The method for producing a Guerbet alcohol according to any one of the items <1> to <13>, wherein the content of the second component contained in the catalyst (A) is preferably 0.0008% by mass or more and 0.8% by mass or less.

<15> The method for producing a Guerbet alcohol according to any one of the items <1> to <14>, wherein the content of the second component contained in the catalyst (A) is preferably 0.001% by mass or more and 0.5% by mass or less.

<16> The method for producing a Guerbet alcohol according to any one of the items <1> to <15>, wherein the content of the second component contained in the catalyst (A) is preferably 0.0025% by mass or more and 0.28% by mass or less.

<17> The method for producing a Guerbet alcohol according to any one of the items <1> to <16>, wherein the content of the second component contained in the catalyst (A) is preferably 0.005% by mass or more and 0.1% by mass or less.

<18> The method for producing a Guerbet alcohol according to any one of the items <1> to <17>, wherein the catalyst (A) is preferably a catalyst including a carrier having the first component and the second component supported thereon.

<19> The method for producing a Guerbet alcohol according to the item <18>, wherein the carrier of the catalyst (A) is preferably at least one kind selected from the group consisting of aluminum oxide, zirconium oxide, and hydrotalcite.

<20> The method for producing a Guerbet alcohol according to the item <18> or <19>, wherein the total content of the first component and the second component contained in the catalyst (A) including the carrier is preferably 6% by mass and 50% by mass or less.

<21> The method for producing a Guerbet alcohol according to any one of the items <18> to <20>, wherein the total content of the first component and the second component contained in the catalyst (A) including the carrier is preferably 8% by mass and 45% by mass or less.

<22> The method for producing a Guerbet alcohol according to any one of the items <18> to <21>, wherein the total content of the first component and the second component contained in the catalyst (A) including the carrier is preferably 10% by mass and 41% by mass or less.

<23> The method for producing a Guerbet alcohol according to any one of the items <1> to <22>, wherein a base catalyst (B) is preferably used with the catalyst (A).

<24> The method for producing a Guerbet alcohol according to the item <23>, wherein the base catalyst (B) is NaOH or KOH.

<25> The method for producing a Guerbet alcohol according to the item <23> or <24>, wherein the amount of the base catalyst (B) per 100 parts by mol in total of the amount of the raw material alcohol is preferably 0.1 part by mol or more and 7 parts by mol or less.

<26> The method for producing a Guerbet alcohol according to any one of the items <23> to <25>, wherein the amount of the base catalyst (B) per 100 parts by mol in total of the amount of the raw material alcohol is preferably 0.2 part by mol or more and 5 parts by mol.

<27> The method for producing a Guerbet alcohol according to any one of the items <23> to <26>, wherein the amount of the base catalyst (B) per 100 parts by mol in total of the amount of the raw material alcohol is preferably 0.3 part by mol or more and 3 parts by mol or less.

<28> The method for producing a Guerbet alcohol according to any one of the items <1> to <27>, wherein the raw material alcohol is preferably a saturated linear primary aliphatic alcohol having 8 or more and 18 or less carbon atoms.

<29> The method for producing a Guerbet alcohol according to any one of the items <1> to <28>, wherein the raw material alcohol is preferably a saturated linear primary aliphatic alcohol having 10 or more and 16 or less carbon atoms.

<30> The method for producing a Guerbet alcohol according to any one of the items <1> to <29>, wherein the raw material alcohol is preferably a saturated linear primary aliphatic alcohol having 11 or more and 15 or less carbon atoms.

<31> The method for producing a Guerbet alcohol according to any one of the items <1> to <30>, wherein the raw material alcohol is preferably a saturated linear primary aliphatic alcohol having 12 or more and 14 or less carbon atoms.

<32> The method for producing a Guerbet alcohol according to any one of the items <1> to <31>, wherein the number of carbon atoms of the Guerbet alcohol is preferably 16 or more and 44 or less.

<33> The method for producing a Guerbet alcohol according to any one of the items <1> to <32>, wherein the number of carbon atoms of the Guerbet alcohol is preferably 18 or more and 40 or less.

<34> The method for producing a Guerbet alcohol according to any one of the items <1> to <33>, wherein the number of carbon atoms of the Guerbet alcohol is preferably 20 or more and 36 or less.

<35> The method for producing a Guerbet alcohol according to any one of the items <1> to <34>, wherein in suspended bed reaction, the amount of the catalyst (A) per 100 parts by mass in total of the amount of the raw material alcohol is preferably 0.01 part by mass or more and 10 parts by mass or less.

<36> The method for producing a Guerbet alcohol according to any one of the items <1> to <35>, wherein in suspended bed reaction, the amount of the catalyst (A) per 100 parts by mass in total of the amount of the raw material alcohol is preferably 0.05 part by mass or more and 5 parts by mass or less.

<37> The method for producing a Guerbet alcohol according to any one of the items <1> to <36>, wherein in suspended bed reaction, the amount of the catalyst (A) per 100 parts by mass in total of the amount of the raw material alcohol is preferably 0.1 part by mass or more and 1 part by mass or less.

EXAMPLES

The present invention will be described in more detail with reference to examples, but the present invention is not limited thereto. The measurements and evaluations in Preparation Examples, Comparative Preparation Examples, Examples, and Comparative Examples were performed in the following manner.

(1) Measurement by ICP Emission Spectroscopy

The first component (Cu) and the second component contained in the catalysts were quantitatively determined by the ICP emission spectroscopy (high frequency inductively coupled plasma emission spectroscopy: ICP-AES, ICP-OES) with an ICP emission spectral analyzer (product name: iCAP 6500 Duo, produced by Thermo Fisher Scientific, Inc.).

The content of Cu contained in the catalyst after supporting the second component was assumed to be the same as the content of Cu contained in the catalysts obtained in Preparation Examples A to E (i.e., the catalyst before supporting the second component) since the amount of the second component used was very small.

(2) Measurement of Average Primary Particle Diameter of Cu

The average primary particle diameter of the first component (Cu) supported on the carrier contained in the catalysts was measured by the pulse method with a catalyst analyzer (product name: BELCAT-B, produced by Nippon Bell Co., Ltd.). After reducing CuO under a 5% H2/Ar gas stream at 150° C. for 4 hours as the pretreatment, 5% $N_2O$/He gas was introduced at 50° C. until reaching saturation, and the average primary particle diameter of Cu was measured from the total gas consumption amount.

The average primary particle diameter of Cu contained in the catalyst after supporting the second component was assumed to be the same as the average primary particle diameter of Cu contained in the catalysts obtained in Preparation Examples A to E (i.e., the catalyst before supporting the second component) since the amount of the second component used was very small.

(3) Measurement of Conversion of Raw Material Alcohol and Yield of Guerbet Alcohol Compound Formed In Examples and Comparative Examples, the solution after completing the reaction was diluted with hexane, and then the products were quantitatively determined by analyzing by gas chromatography (column: Ultra ALLOY-1 (MS/HT) capillary column 30.0 m×250 μm (Frontier Laboratories, Ltd.), detector: FID, injection temperature: 350° C., detector temperature: 350° C., He flow rate: 4.6 mL/min).

The conversion of the raw material alcohol and the yield of the Guerbet alcohol compound formed were calculated from the result of gas chromatography according to the following expressions, respectively. The results are shown in Tables 1 to 4.

The Guerbet alcohol compound means not only the Guerbet alcohol, but also the aldehyde dimer and the allyl alcohol dimer becoming the Guerbet alcohol in the subsequent hydrogenation step.

$$\text{Conversion of raw material alcohol (\%)} = 100 - (\text{residual amount of raw material alcohol (mol)} / \text{charged amount of raw material alcohol (mol)}) \times 100$$

$$\text{Yield of Guerbet alcohol compound formed (\%)} = ((\text{amount of Guerbet alcohol formed (mol)} + \text{amount of aldehyde dimer formed (mol)} + \text{amount of allyl alcohol formed (mol)}) \times 2) / \text{charged amount of raw material alcohol (mol)}) \times 100$$

The Guerbet alcohol in the case where 1-dodecanol (C12) is used as the raw material alcohol is C24 Guerbet alcohol, the Guerbet alcohol in the case where 1-decanol (C10) is used is C20 Guerbet alcohol, and the Guerbet alcohol in the case where 1-hexadecanol (C16) is used is C32 Guerbet alcohol.

Preparation Example A

<Preparation of 21% Cu/$ZrO_2$ by Precipitation Method>

48 g of cupric nitrate trihydrate (produced by Kanto Chemical Co., Inc.) was placed in a 300 mL beaker, to which 246 g of ion exchanged water was added for dissolving to prepare a cupric nitrate aqueous solution. Subsequently, 38 g of sodium carbonate (produced by Fujifilm Wako Pure Chemical Corporation) was placed in another 300 mL beaker, to which 208 g of ion exchanged water was added for dissolving to prepare a sodium carbonate aqueous solution. And further, 50 g of zirconium oxide (product name: RC-100 zirconium oxide, produced by Daiich Kigenso Kagaku Kogyo Co., Ltd. (white powder, median diameter (d50): 1.5 to 4 μm)) was placed in another 2 L beaker, to which 875 g of ion exchanged water was added to prepare a slurry of zirconium oxide.

The cupric nitrate aqueous solution was added dropwise to the slurry of zirconium oxide, and simultaneously the sodium carbonate aqueous solution was added dropwise thereto, while retaining the pH to 7 (20° C.) over 72 minutes. After completing the dropwise addition, a precipitate (i.e., a solid matter including zirconium oxide to be a carrier having a carbonate or a hydroxide of Cu attached thereto) was filtrated under reduced pressure, and the resulting cake was washed with 1 L of ion exchanged water. The cake was subjected three times to an operation including re-slurrying, filtration under reduced pressure, and washing with water, then dried at 120° C. for 18 hours, and further baked in air at 500° C. for 3 hours, so as to provide a $Cu/ZrO_2$ baked material (powder).

The content of Cu contained in the resulting $Cu/ZrO_2$ baked material was 21% by mass, and the average primary particle diameter of Cu was 48 nm.

Preparation Example 1

<Preparation of 21% Cu 0.03% $Rh/ZrO_2$ by Impregnation Method>

0.0074 g of a 25% rhodium(III) nitrate solution (produced by Fujifilm Wako Pure Chemical Corporation) was placed in a 50 mL recovery flask, to which 6 g of ion exchanged water was added for completely dissolving. 2.0 g of the $Cu/ZrO_2$ baked material obtained in Preparation Example A was added thereto, and the mixture was concentrated until the liquid phase disappeared with a rotary evaporator, then dried at 120° C. for 18 hours, and further baked in air at 500° C. for 3 hours, so as to provide a $CuRh/ZrO_2$ baked material (powder) as the catalyst (A).

The content of Cu contained in the resulting $CuRh/ZrO_2$ baked material was 21% by mass, and the average primary particle diameter of Cu was 43 nm.

Preparation Example 2

<Preparation of 21% Cu 0.03% $Pd/ZrO_2$ by Impregnation Method>

A $CuPd/ZrO_2$ baked material (powder) as the catalyst (A) was obtained by performing the same procedure as in Preparation Example 1 except that 0.013 g of a 10% palladium(II) nitrate solution (produced by Sigma Aldrich Japan K.K.) was placed in a 50 mL recovery flask.

Preparation Example 3

<Preparation of 21% Cu 0.03% $Ir/ZrO_2$ by Impregnation Method>

A $CuIr/ZrO_2$ baked material (powder) as the catalyst (A) was obtained by performing the same procedure as in Preparation Example 1 except that 0.0034 g of hexachloroiridic acid(IV) n-hydrate (produced by Fujifilm Wako Pure Chemical Corporation) was placed in a 50 mL recovery flask, to which 15 g of ion exchanged water was added for completely dissolving, and 5.0 g of the $Cu/ZrO_2$ baked material obtained in Preparation Example A was added thereto.

Preparation Example 4

<Preparation of 21% Cu 0.13% $Pt/ZrO_2$ by Impregnation Method>

A $CuPt/ZrO_2$ baked material (powder) as the catalyst (A) was obtained by performing the same procedure as in Preparation Example 1 except that 0.0067 g of hexachloro-platinic acid(IV) hexahydrate (produced by Fujifilm Wako Pure Chemical Corporation) was placed in a 50 mL recovery flask.

Preparation Example 5

<Preparation of 21% Cu 0.03% $Ga/ZrO_2$ by Impregnation Method>

A $CuGa/ZrO_2$ baked material (powder) as the catalyst (A) was obtained by performing the same procedure as in Preparation Example 1 except that 0.0024 g of gallium(III) nitrate n-hydrate (produced by Fujifilm Wako Pure Chemical Corporation) was placed in a 50 mL recovery flask.

Comparative Preparation Example 1

<Preparation of 21% Cu 0.3% $Rh/ZrO_2$ by Impregnation Method>

A $CuRh/ZrO_2$ baked material (powder) as a catalyst for a comparative example was obtained by performing the same procedure as in Preparation Example 1 except that 0.0337 g of a 25% rhodium(III) nitrate solution (produced by Fujifilm Wako Pure Chemical Corporation) was placed in a 50 mL recovery flask, to which 3 g of ion exchanged water was added for completely dissolving, and 1.0 g of the $Cu/ZrO_2$ baked material obtained in Preparation Example A was added thereto.

Preparation Example B

<Preparation of 40% $Cu/ZrO_2$ by Precipitation Method>

76 g of cupric nitrate trihydrate (produced by Kanto Chemical Co., Inc.) was placed in a 500 mL beaker, to which 393 g of ion exchanged water was added for dissolving to prepare a cupric nitrate aqueous solution. Subsequently, 60 g of sodium carbonate (produced by Fujifilm Wako Pure Chemical Corporation) was placed in another 500 mL beaker, to which 333 g of ion exchanged water was added for dissolving to prepare a sodium carbonate aqueous solution. And further, 30 g of zirconium oxide (product name: RC-100 zirconium oxide, produced by Daiich Kigenso Kagaku Kogyo Co., Ltd. (white powder, median diameter (d50): 1.5 to 4 μm)) was placed in another 2 L beaker, to which 525 g of ion exchanged water was added to prepare a slurry of zirconium oxide.

A $Cu/ZrO_2$ baked material (powder) was obtained by performing the same procedure as in Preparation Example A except that the cupric nitrate aqueous solution was added dropwise to the slurry of zirconium oxide, and simultaneously the sodium carbonate aqueous solution was added dropwise thereto, while retaining the pH to 7 (20° C.) over 115 minutes.

The content of Cu contained in the resulting $Cu/ZrO_2$ baked material was 40% by mass, and the average primary particle diameter of Cu was 96 nm.

Preparation Example 6

<Preparation of 40% Cu 0.06% $Rh/ZrO_2$ by Impregnation Method>

A $CuRh/ZrO_2$ baked material (powder) as the catalyst (A) was obtained by performing the same procedure as in Preparation Example 1 except that 0.0138 g of a 25% rhodium(III) nitrate solution (produced by Fujifilm Wako Pure Chemical Corporation) was placed in a 50 mL recovery flask, to which 6 g of ion exchanged water was added for completely dissolving, and 2.0 g of the $Cu/ZrO_2$ baked material obtained in Preparation Example B was added thereto.

Preparation Example 7

<Preparation of 40% Cu 0.01% Rh/ZrO$_2$ by Impregnation Method>

A CuRh/ZrO$_2$ baked material (powder) as the catalyst (A) was obtained by performing the same procedure as in Preparation Example 1 except that 0.023 g of a 25% rhodium(III) nitrate solution (produced by Fujifilm Wako Pure Chemical Corporation) was placed in a 200 mL recovery flask, to which 60 g of ion exchanged water was added for completely dissolving, and 20 g of the Cu/ZrO$_2$ baked material obtained in Preparation Example B was added thereto.

The content of Cu contained in the resulting Cu/ZrO$_2$ baked material was 40% by mass, and the average primary particle diameter of Cu was 114 nm.

Preparation Example C

<Preparation of 11% Cu/ZrO$_2$ by Precipitation Method>

8.5 g of cupric nitrate trihydrate (produced by Kanto Chemical Co., Inc.) was placed in a 50 mL beaker, to which 44 g of ion exchanged water was added for dissolving to prepare a cupric nitrate aqueous solution. Subsequently, 6.7 g of sodium carbonate (produced by Fujifilm Wako Pure Chemical Corporation) was placed in another 50 mL beaker, to which 37 g of ion exchanged water was added for dissolving to prepare a sodium carbonate aqueous solution. And further, 20 g of zirconium oxide (product name: RC-100 zirconium oxide, produced by Daiich Kigenso Kagaku Kogyo Co., Ltd. (white powder, median diameter (d50): 1.5 to 4 μm)) was placed in another 500 mL beaker, to which 350 g of ion exchanged water was added to prepare a slurry of zirconium oxide.

A Cu/ZrO$_2$ baked material (powder) was obtained by performing the same procedure as in Preparation Example A except that the cupric nitrate aqueous solution was added dropwise to the slurry of zirconium oxide, and simultaneously the sodium carbonate aqueous solution was added dropwise thereto, while retaining the pH to 7 (20° C.) over 13 minutes.

The content of Cu contained in the resulting CuRh/ZrO$_2$ baked material was 11% by mass, and the average primary particle diameter of Cu was 23 nm.

Preparation Example 8

<Preparation of 11% Cu 0.05% Rh/ZrO$_2$ by Impregnation Method>

A CuRh/ZrO$_2$ baked material (powder) as the catalyst (A) was obtained by performing the same procedure as in Preparation Example 1 except that 0.011 g of a 25% rhodium (III) nitrate solution (produced by Fujifilm Wako Pure Chemical Corporation) was placed in a 50 mL recovery flask, to which 6 g of ion exchanged water was added for completely dissolving, and 2.0 g of the Cu/ZrO$_2$ baked material obtained in Preparation Example C was added thereto.

Preparation Example 9

<Preparation of 11% Cu 0.0025% Rh/ZrO$_2$ by Impregnation Method>

A CuRh/ZrO$_2$ baked material (powder) as the catalyst (A) was obtained by performing the same procedure as in Preparation Example 1 except that 0.0028 g of a 25% rhodium(III) nitrate solution (produced by Fujifilm Wako Pure Chemical Corporation) was placed in a 200 mL recovery flask, to which 30 g of ion exchanged water was added for completely dissolving, and 10 g of the Cu/ZrO$_2$ baked material obtained in Preparation Example C was added thereto.

The content of Cu contained in the resulting CuRh/ZrO$_2$ baked material was 11% by mass, and the average primary particle diameter of Cu was 22 nm.

Preparation Example D

<Preparation of 21% Cu/Al$_2$O$_3$ by Precipitation Method>

47.5 g of cupric nitrate trihydrate (produced by Kanto Chemical Co., Inc.) was placed in a 300 mL beaker, to which 246 g of ion exchanged water was added for dissolving to prepare a cupric nitrate aqueous solution. Subsequently, 37.5 g of sodium carbonate (produced by Fujifilm Wako Pure Chemical Corporation) was placed in another 300 mL beaker, to which 208 g of ion exchanged water was added for dissolving to prepare a sodium carbonate aqueous solution. And further, 50 g of activated alumina (product name: GP-20, produced by Mizusawa Industrial Chemicals, Ltd.) was placed in another 2 L beaker, to which 875 g of ion exchanged water was added to prepare a slurry of aluminum oxide.

A Cu/Al$_2$O$_3$ baked material (powder) was obtained by performing the same procedure as in Preparation Example A except that the cupric nitrate aqueous solution was added dropwise to the slurry of aluminum oxide, and simultaneously the sodium carbonate aqueous solution was added dropwise thereto, while retaining the pH to 7 (20° C.) over 71 minutes.

The content of Cu contained in the resulting Cu/Al$_2$O$_3$ baked material was 21% by mass, and the average primary particle diameter of Cu was 41 nm.

Preparation Example 10

<Preparation of 21% Cu 0.03% Rh/Al$_2$O$_3$ by Impregnation Method>

A CuRh/Al$_2$O$_3$ baked material (powder) as the catalyst (A) was obtained by performing the same procedure as in Preparation Example 1 except that 0.007 g of a 25% rhodium(III) nitrate solution (produced by Fujifilm Wako Pure Chemical Corporation) was placed in a 50 mL recovery flask, to which 6 g of ion exchanged water was added for completely dissolving, and 2.0 g of the Cu/Al$_2$O$_3$ baked material obtained in Preparation Example E was added thereto.

Preparation Example E

<Preparation of 28% Cu/HT by Precipitation Method>

9.5 g of cupric nitrate trihydrate (produced by Kanto Chemical Co., Inc.) was placed in a 100 mL beaker, to which 49 g of ion exchanged water was added for dissolving to prepare a cupric nitrate aqueous solution. Subsequently, 7.5 g of sodium carbonate (produced by Fujifilm Wako Pure Chemical Corporation) was placed in another 100 mL beaker, to which 42 g of ion exchanged water was added for dissolving to prepare a sodium carbonate aqueous solution. And further, 10 g of synthetic hydrotalcite (product name: Kyowaad 500PL, produced by Kyowa Chemical Industry Co., Ltd.) was placed in another 500 mL beaker, to which 175 g of ion exchanged water was added to prepare a slurry of hydrotalcite.

A Cu/HT baked material (powder) was obtained by performing the same procedure as in Preparation Example A except that the cupric nitrate aqueous solution was added dropwise to the slurry of hydrotalcite, and simultaneously the sodium carbonate aqueous solution was added dropwise thereto, while retaining the pH to 7 (20° C.) over 14 minutes.

The content of Cu contained in the resulting Cu/HT baked material was 28% by mass, and the average primary particle diameter of Cu was 55 nm.

Preparation Example 11

<Preparation of 28% Cu 0.03% Rh/HT by Impregnation Method>

A CuRh/HT baked material (powder) as the catalyst (A) was obtained by performing the same procedure as in Preparation Example 1 except that 0.007 g of a 25% rhodium(III) nitrate solution (produced by Fujifilm Wako Pure Chemical Corporation) was placed in a 50 mL recovery flask, to which 6 g of ion exchanged water was added for completely dissolving, and 2.0 g of the Cu/HT baked material obtained in Preparation Example F was added thereto.

Examples 1-1 to 1-5 and Comparative Example 1-1

Investigation into Second Component

Example 1-1

In a 1 L five-neck glass flask equipped with a stirrer, a thermometer, a nitrogen blowing tube, a sampling tube, and a condenser and a dephlegmator for isolating by-produced water in reaction, 600.0 g (3.22 mol) of 1-dodecanol (C12) (product name: Kalcol 2098, produced by Kao Corporation) as the raw material alcohol, 1.13 g (0.3 part by mol per 100 parts by mol in total of the amount of the raw material alcohol) of a 48% potassium hydroxide aqueous solution (produced by Kanto Chemical Co., Inc.) as the base catalyst (B), and 0.6 g (0.1 part by mass per 100 parts by mass in total of the amount of the raw material alcohol) of the CuRh/ZrO$_2$ baked material prepared in Preparation Example 1 as the catalyst (A) were charged, and the system was heated while bubbling nitrogen gas into the system at a flow rate of 6 L/hr. After the time when the temperature in the system reached 240° C., the flow rate of nitrogen gas was changed to 0.13 L/hr, and the reaction was performed for 8 hours. The results are shown in Table 1.

Examples 1-2 to 1-5 and Comparative Example 1-1

The reaction was performed in the same manner as in Example 1-1 except that the catalyst was changed as shown in Table 1. The results are shown in Table 1.

Examples 2-1 to 2-4 and Comparative Examples 2-1 to 2-3

Investigation into Molar Ratio (Second Component/First Component)
The reaction was performed in the same manner as in Example 1-1 except that the catalyst was changed as shown in Table 2. The results are shown in Table 2.

Examples 3-1 and 3-2 and Comparative Examples 3-1 and 3-2

Investigation into Carrier
The reaction was performed in the same manner as in Example 1-1 except that the catalyst was changed as shown in Table 3. The results are shown in Table 3.

Examples 4-1 and 4-2 and Comparative Examples 4-1 and 4-2

Investigation into Raw Material Alcohol
The reaction was performed in the same manner as in Example 1-1 except that the catalyst and the raw material alcohol were changed as shown in Table 4. The results are shown in Table 4.

TABLE 1

| | | Investigation into Second Component | | | | | |
| --- | --- | --- | --- | --- | --- | --- | --- |
| | | Example 1-1 | Example 1-2 | Example 1-3 | Example 1-4 | Example 1-5 | Comparative Example 1-1 |
| | Raw material alcohol | 1-dodecanol (C12) | 1-dodecanol (C12) | 1-dodecanol (C12) | 1-dodecanol (C12) | 1-dodecanol (C12) | 1-dodecanol (C12) |
| Base catalyst (B) | Kind | KOH | KOH | KOH | KOH | KOH | KOH |
| | Additional amount (part by mol, per 100 parts by mol of raw material alcohol) | 0.3 | 0.3 | 0.3 | 0.3 | 0.3 | 0.3 |
| Catalyst | Kind | Preparation Example 1 | Preparation Example 2 | Preparation Example 3 | Preparation Example 4 | Preparation Example 5 | Preparation Example A |
| | Additional amount (part by mass, per 100 parts by mass of raw material alcohol) | 0.1 | 0.1 | 0.1 | 0.1 | 0.1 | 0.1 |
| First component | Kind | Cu | Cu | Cu | Cu | Cu | Cu |
| | Content (% by mass) | 21 | 21 | 21 | 21 | 21 | 21 |
| | Atomic weight (g/mol) | 63.5 | 63.5 | 63.5 | 63.5 | 63.5 | 63.5 |
| | Mol | 0.3 | 0.3 | 0.3 | 0.3 | 0.3 | 0.3 |
| Second component | Kind | Rh | Pd | Ir | Pt | Ga | — |
| | Content (% by mass) | 0.03 | 0.03 | 0.03 | 0.13 | 0.03 | — |
| | Atomic weight (g/mol) | 102.9 | 106.4 | 192.2 | 195.1 | 69.7 | — |
| | Mol | 0.00029 | 0.00028 | 0.00016 | 0.00067 | 0.00043 | — |
| Carrier | Kind | ZrO$_2$ | ZrO$_2$ | ZrO$_2$ | ZrO$_2$ | ZrO$_2$ | ZrO$_2$ |
| Molar ratio (second component/first component) | | 0.0009 | 0.0009 | 0.0005 | 0.0020 | 0.0013 | 0 |

TABLE 1-continued

| | Investigation into Second Component | | | | | | |
|---|---|---|---|---|---|---|---|
| | | Example 1-1 | Example 1-2 | Example 1-3 | Example 1-4 | Example 1-5 | Comparative Example 1-1 |
| Reaction condition | Reaction temperature (° C.) | 240 | 240 | 240 | 240 | 240 | 240 |
| | Reaction time (h) | 8 | 8 | 8 | 8 | 8 | 8 |
| Evaluation | Conversion of raw material alcohol (%) | 71 | 67 | 67 | 69 | 65 | 61 |
| | Yield of Guerbet alcohol compound formed (%) | 52 | 48 | 49 | 49 | 47 | 46 |
| | Enhancement rate of conversion (%) | 16 | 10 | 10 | 13 | 7 | — |
| | Enhancement rate of yield (%) | 13 | 4 | 7 | 7 | 2 | — |

TABLE 2

| | | Investigation into Molar Ratio (Second Component/First Component) | | | | | | | |
|---|---|---|---|---|---|---|---|---|---|
| | | Example 2-1 | Example 2-2 | Comparative Example 2-1 | Example 2-3 | Example 2-4 | Comparative Example 2-2 | Comparative Example 1-1 | Comparative Example 2-3 |
| | Raw material alcohol | 1-dodecanol (C12) | 1-dodecanol (C12) | 1-dodecanol (C12) | 1-dodecanol (C12) | 1-dodecanol (C12) | 1-dodecanol (C12) | 1-dodecanol (C12) | 1-dodecanol (C12) |
| Base catalyst (B) | Kind | KOH | KOH | KOH | KOH | KOH | KOH | KOH | KOH |
| | Additional amount (part by mol, per 100 parts by mol of raw material alcohol) | 0.3 | 0.3 | 0.3 | 0.3 | 0.3 | 0.3 | 0.3 | 0.3 |
| Catalyst | Kind | Preparation Example 6 | Preparation Example 7 | Preparation Example B | Preparation Example 8 | Preparation Example 9 | Preparation Example C | Preparation Example A | Comparative Preparation Example 1 |
| | Additional amount (part by mass, per 100 parts by mass of raw material alcohol) | 0.1 | 0.1 | 0.1 | 0.1 | 0.1 | 0.1 | 0.1 | 0.1 |
| First component | Kind | Cu | Cu | Cu | Cu | Cu | Cu | Cu | Cu |
| | Content (% by mass) | 40 | 40 | 40 | 11 | 11 | 11 | 21 | 21 |
| | Atomic weight (g/mol) | 63.5 | 63.5 | 63.5 | 63.5 | 63.5 | 63.5 | 63.5 | 63.5 |
| | Mol | 0.6 | 0.6 | 0.6 | 0.2 | 0.2 | 0.2 | 0.3 | 0.3 |
| Second component | Kind | Rh | Rh | — | Rh | Rh | — | — | Rh |
| | Content (% by mass) | 0.06 | 0.01 | — | 0.05 | 0.0025 | — | — | 0.3 |
| | Atomic weight (g/mol) | 102.9 | 102.9 | — | 102.9 | 102.9 | — | — | 102.9 |
| | Mol | 0.00058 | 0.00010 | — | 0.00049 | 0.00002 | — | — | 0.00292 |
| Carrier | Kind | $ZrO_2$ | $ZrO_2$ | $ZrO_2$ | $ZrO_2$ | $ZrO_2$ | $ZrO_2$ | $ZrO_2$ | $ZrO_2$ |
| | Molar ratio (second component/first component) | 0.0009 | 0.0002 | 0 | 0.0028 | 0.0001 | 0 | 0 | 0.0088 |
| Reaction condition | Reaction temperature (° C.) | 240 | 240 | 240 | 240 | 240 | 240 | 240 | 240 |
| | Reaction time (h) | 8 | 8 | 8 | 8 | 8 | 8 | 8 | 8 |
| Evaluation | Conversion of raw material alcohol (%) | 67 | 65 | 61 | 62 | 58 | 53 | 61 | 48 |
| | Yield of Guerbet alcohol compound formed (%) | 49 | 47 | 46 | 45 | 44 | 42 | 46 | 37 |
| | Enhancement rate of conversion (%) | 10 | 7 | — | 17 | 9 | — | — | −21 |
| | Enhancement rate of yield (%) | 7 | 2 | — | 7 | 5 | — | — | −20 |

TABLE 3

Investigation into Carrier

| | | Example 1-1 | Comparative Example 1-1 | Example 3-1 | Comparative Example 3-1 | Example 3-2 | Comparative Example 3-2 |
|---|---|---|---|---|---|---|---|
| | Raw material alcohol | 1-dodecanol (C12) | 1-dodecanol (C12) | 1-dodecanol (C12) | 1-dodecanol (C12) | 1-dodecanol (C12) | 1-dodecanol (C12) |
| Base catalyst (B) | Kind | KOH | KOH | KOH | KOH | KOH | KOH |
| | Additional amount (part by mol, per 100 parts by mol of raw material alcohol) | 0.3 | 0.3 | 0.3 | 0.3 | 0.3 | 0.3 |
| Catalyst | Kind | Preparation Example 1 | Preparation Example A | Preparation Example 10 | Preparation Example D | Preparation Example 11 | Preparation Example E |
| | Additional amount (part by mass, per 100 parts by mass of raw material alcohol) | 0.1 | 0.1 | 0.1 | 0.1 | 0.1 | 0.1 |
| First component | Kind | Cu | Cu | Cu | Cu | Cu | Cu |
| | Content (% by mass) | 21 | 21 | 21 | 21 | 28 | 28 |
| | Atomic weight (g/mol) | 63.5 | 63.5 | 63.5 | 63.5 | 63.5 | 63.5 |
| | Mol | 0.3 | 0.3 | 0.3 | 0.3 | 0.4 | 0.4 |
| Second component | Kind | Rh | — | Rh | — | Rh | — |
| | Content (% by mass) | 0.03 | — | 0.03 | — | 0.03 | — |
| | Atomic weight (g/mol) | 102.9 | — | 102.9 | — | 102.9 | — |
| | Mol | 0.00029 | — | 0.00029 | — | 0.00029 | — |
| Carrier | Kind | $ZrO_2$ | $ZrO_2$ | $Al_2O_3$ | $Al_2O_3$ | HT | HT |
| | Molar ratio (second component/first component) | 0.0009 | 0 | 0.0009 | 0 | 0.0007 | 0 |
| Reaction condition | Reaction temperature (° C.) | 240 | 240 | 240 | 240 | 240 | 240 |
| | Reaction time (h) | 8 | 8 | 8 | 8 | 8 | 8 |
| Evaluation | Conversion of raw material alcohol (%) | 71 | 61 | 65 | 61 | 73 | 70 |
| | Yield of Guerbet alcohol compound formed (%) | 52 | 46 | 48 | 46 | 53 | 50 |
| | Enhancement rate of conversion (%) | 16 | — | 7 | — | 4 | — |
| | Enhancement rate of yield (%) | 13 | — | 4 | — | 6 | — |

TABLE 4

Investigation into Raw Material Alcohol

| | | Example 4-1 | Comparative Example 4-1 | Example 1-3 | Comparative Example 1-1 | Example 4-2 | Comparative Example 4-2 |
|---|---|---|---|---|---|---|---|
| | Raw material alcohol | 1-decanol (C10) | 1-decanol (C10) | 1-dodecanol (C12) | 1-dodecanol (C12) | 1-hexadecanol (C16) | 1-hexadecanol (C16) |
| Base catalyst (B) | Kind | KOH | KOH | KOH | KOH | KOH | KOH |
| | Additional amount (part by mol, per 100 parts by mol of raw material alcohol) | 0.3 | 0.3 | 0.3 | 0.3 | 0.3 | 0.3 |
| Catalyst | Kind | Preparation Example 3 | Preparation Example A | Preparation Example 3 | Preparation Example A | Preparation Example 3 | Preparation Example A |
| | Additional amount (part by mass, per 100 parts by mass of raw material alcohol) | 0.1 | 0.1 | 0.1 | 0.1 | 0.1 | 0.1 |
| First component | Kind | Cu | Cu | Cu | Cu | Cu | Cu |
| | Content (% by mass) | 21 | 21 | 21 | 21 | 21 | 21 |
| | Atomic weight (g/mol) | 63.5 | 63.5 | 63.5 | 63.5 | 63.5 | 63.5 |
| | Mol | 0.3 | 0.3 | 0.3 | 0.3 | 0.3 | 0.3 |
| Second component | Kind | Ir | — | Ir | — | Ir | — |
| | Content (% by mass) | 0.03 | — | 0.03 | — | 0.03 | — |
| | Atomic weight (g/mol) | 192.2 | — | 192.2 | — | 192.2 | — |
| | Mol | 0.00016 | — | 0.00016 | — | 0.00016 | — |
| Carrier | Kind | $ZrO_2$ | $ZrO_2$ | $ZrO_2$ | $ZrO_2$ | $ZrO_2$ | $ZrO_2$ |
| | Molar ratio (second component/first component) | 0.0005 | 0 | 0.0005 | 0 | 0.0005 | 0 |

TABLE 4-continued

| | | Investigation into Raw Material Alcohol | | | | | |
| --- | --- | --- | --- | --- | --- | --- | --- |
| | | Example 4-1 | Comparative Example 4-1 | Example 1-3 | Comparative Example 1-1 | Example 4-2 | Comparative Example 4-2 |
| Reaction condition | Reaction temperature (° C.) | 240 | 240 | 240 | 240 | 240 | 240 |
| | Reaction time (h) | 8 | 8 | 8 | 8 | 8 | 8 |
| Eval-uation | Conversion of raw material alcohol (%) | 56 | 47 | 67 | 61 | 53 | 47 |
| | Yield of Guerbet alcohol compound formed (%) | 42 | 36 | 49 | 46 | 39 | 33 |
| | Enhancement rate of conversion (%) | 19 | — | 10 | — | 13 | — |
| | Enhancement rate of yield (%) | 17 | — | 7 | — | 18 | — |

(Summary of Results 1: Investigation into Second Component)

It was found that Examples 1-1 to 1-5 using the catalyst (A) containing Rh, Pd, Ir, Pt, or Ga as the second component were excellent in the effect of enhancing the yield of the Guerbet alcohol compound formed, as compared to Comparative Example 1-1 using the catalyst having the same content of the first component but containing no second component. It was found that among these, Example 1-1 using the catalyst (A) containing Rh as the second component was further excellent in the effect.

(Summary of Results 2: Investigation into Molar Ratio (Second Component/First Component)

It was found that Examples 2-1 and 2-2 using the catalyst (A) having a molar ratio (second component/first component) within the range of the present invention were excellent in the effect of enhancing the yield of the Guerbet alcohol compound formed, as compared to Comparative Example 2-1 using the catalyst having the same content of the first component but containing no second component.

It was found that Examples 2-3 and 2-4 using the catalyst (A) having a molar ratio (second component/first component) within the range of the present invention were excellent in the effect of enhancing the yield of the Guerbet alcohol compound formed, as compared to Comparative Example 2-2 using the catalyst having the same content of the first component but containing no second component.

It was found that Example 1-1 using the catalyst (A) having a molar ratio (second component/first component) within the range of the present invention was excellent in the effect of enhancing the yield of the Guerbet alcohol compound formed, as compared to Comparative Example 2-3 using the catalyst having the same content of the first component but having a molar ratio (second component/first component) exceeding the range of the present invention.

(Summary of Results 3: Investigation into Carrier)

It was found that Example 3-1 using the catalyst (A) including $Al_2O_3$ as the carrier was excellent in the effect of enhancing the yield of the Guerbet alcohol compound formed, as compared to Comparative Example 3-1 using the catalyst having the same content of the first component but containing no second component.

It was found that Example 3-2 using the catalyst (A) including HT as the carrier was excellent in the effect of enhancing the yield of the Guerbet alcohol compound formed, as compared to Comparative Example 3-2 using the catalyst having the same content of the first component but containing no second component.

(Summary of Results 4: Investigation into Raw Material Alcohol)

It was found that Example 4-1 using 1-decanol (C10) as the raw material alcohol was excellent in the effect of enhancing the yield of the Guerbet alcohol compound formed, as compared to Comparative Example 4-1 using the catalyst having the same content of the first component but containing no second component.

It was found that Example 4-2 using 1-hexadecanol (C16) as the raw material alcohol was excellent in the effect of enhancing the yield of the Guerbet alcohol compound formed, as compared to Comparative Example 4-2 using the catalyst having the same content of the first component but containing no second component.

It was found that among Examples 1-3, 4-1, and 4-2 using 1-decanol (C10), 1-dodecanol (C12), and 1-hexadecanol (C16) as the raw material alcohol, Example 1-3 using 1-dodecanol (C12) as the raw material alcohol was further excellent in the effect.

The invention claimed is:

1. A method for producing a Guerbet alcohol, comprising reacting a raw material alcohol having 8 or more and 22 or less carbon atoms, in the presence of a catalyst (A) consisting of a first component and a second component below, having a molar ratio of the second component with respect to the first component (second component/first component) of 0.0001 or more and 0.004 or less:
   first component: copper, and
   second component: one kind selected from the group consisting of elements that are elements belonging to Groups 9 to 13 in the fourth to sixth periods of the periodic table, except copper.

2. The method for producing a Guerbet alcohol according to claim 1, wherein the second component of the catalyst (A) is one kind selected from gallium (Ga), rhodium (Rh), palladium (Pd), iridium (Ir), and platinum (Pt).

3. The method for producing a Guerbet alcohol according to claim 1, wherein the catalyst (A) is a catalyst (A) including a carrier having the first component and the second component supported thereon.

4. The method for producing a Guerbet alcohol according to claim 3, wherein the carrier of the catalyst (A) is at least one kind selected from the group consisting of aluminum oxide, activated carbon, titanium oxide, zirconium oxide, zeolite, cerium oxide, and hydrotalcite.

5. The method for producing a Guerbet alcohol according to claim 1, wherein a content of the first component contained in the catalyst (A) is 6% by mass or more and 50% by mass or less.

6. The method for producing a Guerbet alcohol according to claim 1, wherein in suspended bed reaction, an amount of the catalyst (A) per 100 parts by mass in total of the amount of the raw material alcohol is 0.01 part by mass or more and 10 parts by mass or less.

7. The method for producing a Guerbet alcohol according to claim 1, wherein a base catalyst (B) is used with the catalyst (A).

8. The method for producing a Guerbet alcohol according to claim 7, wherein an amount of the base catalyst (B) per 100 parts by mol in total of the amount of the raw material alcohol is 0.1 part by mol or more and 7 parts by mol or less.

9. The method for producing a Guerbet alcohol according to claim 1, wherein the raw material alcohol is a saturated linear primary aliphatic alcohol having 8 or more and 18 or less carbon atoms.

10. A catalyst used for a method for producing a Guerbet alcohol, comprising a first component and a second component below, having a molar ratio of the second component with respect to the first component (second component/first component) of 0.0001 or more and 0.004 or less:

first component: copper, and second component: gallium (Ga), palladium (Pd), iridium (Ir), or platinum (Pt).

\* \* \* \* \*